United States Patent
Sakamoto et al.

(10) Patent No.: US 11,504,306 B2
(45) Date of Patent: Nov. 22, 2022

(54) DENTAL GLASS IONOMER CEMENT COMPOSITION

(71) Applicant: SHOFU INC., Kyoto (JP)

(72) Inventors: Shuji Sakamoto, Kyoto (JP); Shun Shimosoyama, Kyoto (JP); Katsuya Kimoto, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 17/032,212

(22) Filed: Sep. 25, 2020

(65) Prior Publication Data
US 2021/0212906 A1    Jul. 15, 2021

(30) Foreign Application Priority Data

Sep. 26, 2019  (JP) .............................. JP2019-175362

(51) Int. Cl.
*A61K 6/889* (2020.01)
*A61K 6/77* (2020.01)
*A61C 5/00* (2017.01)

(52) U.S. Cl.
CPC ................ *A61K 6/889* (2020.01); *A61K 6/77* (2020.01); *A61C 5/00* (2013.01)

(58) Field of Classification Search
CPC ...................................................... A61K 6/889
See application file for complete search history.

(56) References Cited

U.S. PATENT DOCUMENTS

| | | | | |
|---|---|---|---|---|
| 5,227,413 | A | * 7/1993 | Mitra | ............... A61K 6/889 523/116 |
| 5,925,715 | A | * 7/1999 | Mitra | ............... A61K 6/30 525/293 |
| 7,851,515 | B2 | 12/2010 | Salz et al. | |
| 2004/0254260 | A1 | 12/2004 | Mikulla et al. | |
| 2018/0237567 | A1 | 8/2018 | Klee et al. | |

FOREIGN PATENT DOCUMENTS

| JP | 07-053645 | 6/1995 |
|---|---|---|
| JP | 2004-527464 | 9/2004 |
| WO | 2009/129221 | 10/2009 |

OTHER PUBLICATIONS

Extended European Search Report dated Mar. 22, 2021, in corresponding European Patent Application No. 20197241.1.
Communication pursuant to Article 94(3) EPC dated Feb. 16, 2022, in corresponding European Patent Application No. 20197241.1.

* cited by examiner

*Primary Examiner* — Michael F Pepitone
(74) *Attorney, Agent, or Firm* — Wenderoth, Lind & Ponack, L.L.P.

(57) ABSTRACT

A dental glass ionomer cement composition that exhibits high mechanical properties. In particular, the dental glass ionomer cement composition of the present disclosure comprising (a) non-crosslinked polyalkenoic acid, (b) water, (c) crosslinked polyalkenoic acid: 0.01 to 10 wt. %, and (d) acid-reactive glass powder, exhibits extremely high compressive strength by including the crosslinked polyalkenoic acid in the specified content range.

4 Claims, No Drawings

DENTAL GLASS IONOMER CEMENT COMPOSITION

CROSS-REFERENCE TO RELATED APPLICATIONS

This application is based on and claims the benefit of priority from Japanese Patent Application Serial No. 2019-175362 (filed on Sep. 26, 2019), the contents of which are hereby incorporated by reference in their entirety.

BACKGROUND OF THE INVENTION

Field of the Invention

The present disclosure relates to a dental glass ionomer cement. More specifically, the present disclosure relates a dental glass ionomer cement for filling or a dental glass ionomer cement for luting which exhibit high mechanical property.

Description of the Related Art

In a dental practice, in order to restore aesthetically and functionally the tooth in which a form was partially lost by caries, breakages and the like, a direct restorative in which a dental glass ionomer cement for filling is filled into the tooth and an indirect restorative in which a dental prosthesis device is adhered or bonded to a tooth by using a dental glass ionomer cement for luting has been performed.

The dental glass ionomer cement represented by the dental glass ionomer cement for filling and the dental glass ionomer cement for luting has high biocompatibility and releases fluoride ion which can be expected to prevent secondary caries. However, it is inferior in mechanical properties such as compressive strength as compared with dental resin materials such as a dental composite resin for filling and a dental adhesive resin cement. Therefore, its use is limited to such as filling and restoring for a part where pressure at the time of occlusion is not directly applied and gradual filling and restoring. Under these circumstances, improvement of mechanical properties of the dental glass ionomer cement has been desired.

In order to solve this problem, a dental glass ionomer cement composition containing polyalkenoic acid having a special structure has been proposed. For example, in Patent Document 1 and Patent Document 2, a dental glass ionomer cement composition containing a star-shaped or comb-shaped polyalkenoic acid having a cross-linking point or a branching point in the molecule has been proposed.

RELEVANT REFERENCES

Patent Literature

[Patent Literature 1] Japanese Examined Patent Application Publication No. H7-53645
[Patent Literature 2] Japanese Unexamined Patent Application Publication (Translation of PCT Application) No. 2004-527464

SUMMARY OF THE INVENTION

Technical Problem

However, mechanical properties of the dental glass ionomer cement compositions of Patent Document 1 and Patent Document 2 are still insufficient, and there is room for improvement. Therefore, it is an object of the present disclosure to provide a dental glass ionomer cement composition having significantly improved mechanical properties as compared with the prior art.

Solution to Problem

As a result of intensive studies in view of the above problems, it has been found by the present inventors that extremely high compressive strength can be exhibited by compounding crosslinked polyalkenic acid in a specific range in a dental glass ionomer cement composition containing non-crosslinked polyalkenoic acid, water, crosslinked polyalkenoic acid and acid-reactive glass powder and the present invention have been completed.

That is, the present disclosure provides a dental glass ionomer cement composition, comprising
(a) non-crosslinked polyalkenoic acid,
(b) water,
(c) crosslinked polyalkenoic acid: 0.01 to 10 wt. %, and
(d) acid-reactive glass powder.

In the above describe dental glass ionomer cement composition, it is preferable that the (c) crosslinked polyalkenic acid is a crosslinked polyacrylic acid.

In the above describe dental glass ionomer cement composition, it is preferable that based on the total amount of the composition,
(a) non-crosslinked polyalkenoic acid: 5 to 20 wt. %,
(b) water: 10 to 25 wt. %,
(c) crosslinked polyalkenoic acid: 0.01 to 10 wt. %, and
(d) acid-reactive glass powder: 60 to 80 wt. %.

Advantageous Effects of Invention

Since mechanical properties of the dental glass ionomer cement composition of the present disclosure are significantly improved as compared with the prior art, the dental glass ionomer cement composition of the present disclosure can be applied to restorative sites where occlusal pressure is applied, for example.

DETAILED DESCRIPTION OF THE PREFERRED EMBODIMENTS

Hereinafter, each components in the dental glass ionomer cement composition of the present disclosure is described in detail.

Any non-crosslinked polyalkenoic acids can be used without any limitation as the (a) non-crosslinked polyalkenoic acid that can be used in the dental glass ionomer cement composition of the present disclosure, as long as it is a homopolymer or copolymer of alkenoic acid having at least one or more carboxyl groups in the molecule such as unsaturated monocarboxylic acid, unsaturated dicarboxylic acid, unsaturated tricarboxylic acid and the like, and does not have a cross-linking point in the molecule. Further, the (a) non-crosslinked polyalkenoic acid may be a copolymer of a non-crosslinked polymerizable monomer having no acidic group in the molecule and an alkenoic acid, without any problems.

Specific examples of an alkenoic acid which may be used for obtaining the (a) non-crosslinked polyalkenoic acid are not limited to, but include (meth)acrylic acid, 2-chloro acrylic acid, 3-chloro (meth)acrylic acid, 2-cyano acrylic acid, aconitic acid, mesaconic acid, maleic acid, maleic anhydride, itaconic acid, itaconic anhydride, fumaric acid, glutaconic acid, citraconic acid, utraconic acid, 1-buten-1, 2,4-tricarboxylic acid, and 3-buten-1,2,3-tricarboxylic acid. It is preferable to use a (a) non-crosslinked polyalkenoic acid synthesized from only acrylic acid as a starting material or a (a) non-crosslinked polyalkenoic acid synthesized from two or more kinds of starting materials such as acrylic acid and maleic acid, acrylic acid and maleic anhydride, acrylic acid and itaconic acid, and acrylic acid and 3-butene-1,2,3-tricarboxylic acid.

The polymerization method used for obtaining various non-crosslinked polyalkenoic acids is not particularly limited, and a polymer polymerized by any methods such as solution polymerization, suspension polymerization, emulsion polymerization or the like, may be used without any limitations. In addition, a polymerization initiator and a chain transfer agent used at the time of synthesis of a polymer may be appropriately selected in order to obtain a desired polymer. The (a) non-crosslinked polyalkenoic acid obtained by such way can be used alone, or in a combination of a few kinds.

A weight average molecular weight of the polymer of the (a) non-crosslinked polyalkenic acid is preferably within a range of 30,000 to 300,000. Herein, the weight average molecular weight means the average molecular weight which is calculated based on molecular weight distribution measured by gel permeation chromatography. When the weight average molecular weight of the (a) non-crosslinked polyalkenoic acid is less than 30,000, the mechanical characteristic may decrease. When the weight average molecular weight of the (a) non-crosslinked polyalkenoic acid is more than 300,000, viscosity of the mixture may increase and operability may worsen. Further there is a case where operation time may become short.

It is preferable that a content of the (a) non-crosslinked polyalkenoic acid is within a range of 5 to 20 wt. % based on the whole dental glass ionomer cement composition. When the content of the (a) non-crosslinked polyalkenoic acid is less than 5 wt. %, there is a case where the mechanical characteristic decrease. When the content of the (a) non-crosslinked polyalkenoic acid is more than 20 wt. %, there is a case where viscosity of the mixture increase and operability worsen. Further there is a case where operation time may become short.

The (b) water that can be used in the dental glass ionomer cement composition of the present disclosure is an essential component which functions as a solvent for dissolving the (a) non-crosslinked polyalkenoic acid and the (c) cross-linked polyalkenoic acid described later, diffuses metal ions eluted from the (d) acid-reactive glass powder described later, and induces a cross-linking reaction with the (a) non-crosslinked polyalkenoic acid and the (c) crosslinked polyalkenoic acid.

Any water can be used as the (b) water as long as it does not contain impurities adversely affecting on the curability and mechanical characteristic of the dental glass ionomer cement composition without any limitations. Specifically, it is preferably to use distilled water or ion-exchanged water.

It is preferable that a content of the (b) water is within a range of 10 to 25 wt. % based on the whole dental glass ionomer cement composition. When the content of the (b) water is less than 10 wt. %, there is a case where viscosity of the mixture increase and operability worsen. Further there is a case where operation time may become short. When the content of the (b) water is more than 25 wt. %, there is a case where the mechanical characteristic decrease.

Any crosslinked polyalkenoic acid can be used without any limitations as the (c) crosslinked polyalkenoic acid that can be used in the dental glass ionomer cement composition of the present disclosure, as long as it is a copolymer of an alkenoic acid having at least one or more carboxyl groups in the molecule and a cross-linking agent described later, and has at least one or more cross-linking points in the molecule. Further, as the alkenoic acid used at this, the same alkenoic acid used to obtain the above-mentioned (a) non-crosslinked polyalkenoic acid can be used. Further, the (c) crosslinked polyalkenoic acid may be a copolymer of a non-crosslinkable polymerizable monomer having no acidic group in the molecule, an alkenoic acid, and a cross-linking agent.

Among them, it is preferable to use (c) crosslinked polyalkenoic acid synthesized by copolymerizing only acrylic acid with a cross-linking agent, (c) crosslinked polyalkenoic acid synthesized by copolymerizing two or more kinds such as acrylic acid and maleic acid, acrylic acid and maleic anhydride, acrylic acid and itaconic acid, acrylic acid and 3-butene-1,2,3-tricarboxylic acid with a cross-linking agent, and since it can be easily synthesized, it is more preferable to use a (c) crosslinked polyalkenoic acid synthesized by copolymerizing only acrylic acid with a cross-linking agent.

As the cross-linking agent which may be used for obtaining the (c) crosslinked polyalkenoic acid, any cross-linking agents can be used without any limitations as long as it has at least two or more unsaturated groups in the molecule. In addition, any cross-linking agents may be used regardless of the number or the type of radical polymerizable unsaturated groups (bifunctional groups, trifunctional or tetrafunctional or higher) of the cross-linking agent. Specific examples of the unsaturated group of the cross-linking agent include a (meth)acryloyl group, a styryl group, a vinyl group, and an aryl group. It is preferable that cross-linking agent has a (meth)acryloyl group among these unsaturated groups.

Specific examples of the cross-linking agent which may be used for obtaining the (c) crosslinked polyalkenoic acid include ethyleneglycol di(meth)acrylate, diethyleneglycol di(meth)acrylate, triethyleneglycol di(meth)acrylate, tetraethyleneglycol di(meth)acrylate, polyethyleneglycol di(meth)acrylate, neopentylglycol di(meth)acrylate, propropyleneglycol di(meth)acrylate, dipropyleneglycol di(meth)acrylate, tripropyleneglycol di(meth)acrylate, tricyclodecane dimethanol di(meth)acrylate, 1,3-butanediol di(meth)acrylate, 1,4-butandiol di(meth)acrylate, 1,6-hexanediol di(meth)acrylate, 1,9-nonanediol di(meth)acrylate, 1,10-decanediol di(meth)acrylate, 2-hydroxypropyl-1,3-di(meth)acrylate (CDMA), trimetylolprop an tri(meth)acrylate, pentaerythritol tetra(meth)acrylate, dipentaerythritol hexa(meth)acrylate, dipentaerythritol penta(meth)acrylate, ethyleneglycol diallylether, diethyleneglycol diallylether, triethyleneglycol diallylether, tetraethyleneglycol diallylether, 1,5-hexadiene-3,4-diol, diallyl ether, glycerol-α,α'-diallyl ether and the like, but are not limited to.

It is preferable that a content of the cross-linking agent in the (c) crosslinked polyalkenoic acid is within a range of 0.0001 to 10 wt. %, more preferably within a range of 0.001 to 5 wt. %. When the content of the cross-linking agent is less than 0.0001 wt. %, there is a case where it is not possible to obtain the effect of the present disclosure which is to exhibit high mechanical properties. When the content of the cross-linking agent exceeds 10 wt. %, there is a case that viscosity of the mixed material may become very higher to worsen operability. Further, there is a case the mechanical characteristic of the set product may be too low to cause a problem in durability.

The method of polymerizing the above described alkenoic acid and the cross-linking agent is not particularly limited, and a polymer polymerized by any methods such as solution polymerization, suspension polymerization, emulsion polymerization or the like, may be used without any limitation. In addition, a polymerization initiator and a chain transfer agent used at the time of synthesis of a polymer may be appropriately selected in order to obtain a desired polymer. The (c) crosslinked polyalkenoic acid obtained by such way can be used alone, or in a combination of a few kinds.

A content of the (c) crosslinked polyalkenoic acid must be within a range of 0.01 to 10 wt. % based on the whole dental glass ionomer cement composition. The content is preferably within a range of 0.05 to 5 wt. %, more preferably within a range of 0.1 to 3 wt. %. When the content of the (c) crosslinked polyalkenoic is less than 0.01 wt. %, it is not possible to obtain the effect of the present disclosure which is to exhibit high mechanical properties. When the content exceeds 10 wt. %, viscosity of the mixed material may become very higher to worsen operability. Further, the mechanical characteristic of set product decrease to cause problems in durability.

The (d) acid-reactive glass powder that can be used in the dental glass ionomer cement composition of the present disclosure needs to contain an acid-reactive element such as metal element, and fluorine element. Because the (d) acid-reactive glass powder includes an acid reactive element, the acid-base reaction of the (d) acid reactive glass powder with the acid group contained in the (a) non-crosslinked polyalkenoic acid and (c) crosslinked polyalkenoic acid progresses in the presence of water. Specific examples of an acid reactive element include sodium, potassium, calcium, strontium, barium, lanthanum, aluminum and zinc, but are not limited thereto. One or two or more kinds of these acid reactive element may be contained and the content thereof is not particularly limited.

Further, it is preferable that the (d) acid reactive glass powder includes an X-ray impermeable element in order to impart X-ray contrast property to the dental glass ionomer cement composition of the present disclosure. Specific examples of an X-ray impermeable element include strontium, lanthanum, zirconium, titanium, yttrium, ytterbium, tantalum, tin, tellurium, tungsten and bismuth, but are not limited thereto. In addition, other element contained in the (d) acid reactive glass powder is not particularly limited and the (d) acid reactive glass powder in the present disclosure may include various elements.

Specific examples of the (d) acid reactive glass powder include aluminosilicate glass, borosilicate glass, aluminoborate glass, boro aluminosilicate glass, phosphate glass, borate glass, silica glass wherein the above described acid reactive element, fluorine element and X-ray impermeable element are contained, but are not limited thereto.

Further, a particle shape of the (d) acid reactive glass powder is not particularly limited, but arbitral particle shapes such as spherical, needle-like, plate-like, ground-like, and scaly-shape may be used without any limitation. These (d) acid reactive glass powder may be used alone or in combination of two or more thereof.

A preparing process of the (d) acid reactive glass powder is not particularly limited, but (d) acid reactive glass powder prepared by any process such as a melting process, a vapor phase process and a sol-gel process may be used without any problem. Among them, the (d) acid reactive glass powder prepared by a melting method or a sol-gel method which can easily control a kind of element and the content thereof is preferably used.

The (d) acid reactive glass powder may be ground to use in order to obtain a desirable average particle diameter. A grinding method is not particularly limited, but an acid-reactive element-containing glass powder obtained by grinding which use any of wet or dry grinding methods may be used. Specifically, the (d) acid reactive glass powder may be ground by a high speed rotating mill such as a hammer mill and a turbo-mill, a container driving medium mill such as a ball mill and a vibration mill, a medium stirring mill such as a sand grinder and attritor, and a jet mill and the like to appropriately adjust the average particle diameter according to the intended use or purpose of use of the dental glass ionomer cement composition of the present disclosure.

For example, when the dental glass ionomer cement composition of the present disclosure is used as a material for filling or abutment building, because high mechanical strength is required, the (d) acid-reactive glass powder has preferably the average particle diameter within a range of 0.01 to 30.0 μm, more preferably within a range of 0.01 to 10.0 μm.

In addition, when the dental glass ionomer cement composition of the present disclosure is used as a material for luting, because a thin film thickness is required, the (d) acid-reactive glass powder has preferably the average particle diameter within a range of 0.01 to 10.0 μm, more preferably within a range of 0.01 to 5.0 μm.

When the average particle diameter of the (d) acid-reactive glass powder is less than 0.01 μm, the surface area of the acid-reactive glass powder increases and it becomes impossible to contain the acid-reactive glass powder in a large amount in the composition, there is a risk that deterioration in mechanical strength may be caused. In addition, there is a case that the viscosity of the mixture is high and the operability deteriorates.

In case of using as a material for filling, when the average particle diameter of the (d) acid-reactive glass powder exceeds 30.0 μm, the surface of the material after polishing becomes rough, therefore coloring and color change may be caused. Further, in case of using as a material for luting, when the average particle diameter of the (d) acid-reactive glass powder exceeds 10.0 μm, because the film thickness becomes thick, there is a case that the attached dental prosthesis device is lifted and therefore the intended of the prosthesis device fit cannot be obtained.

The (d) acid reactive glass powder may be treated with various surface treatments, heat treatment, aggregating treatment in a liquid phase or a vapor phase, microcapsulation in which particle is enclosed with an organic substance, grafting in which a surface is functionalized with an organic substance and the like to such a range that the acid-base reaction of the (d) acid reactive glass powder with the acid group contained in the (a) non-crosslinked polyalkenoic acid and (c) crosslinked polyalkenoic acid is not influenced, in order to adjust operability, curing characteristics, mechanical characteristics and the like of the dental glass ionomer cement composition of the present disclosure. These treatments can be performed alone, or in a combination of a few kinds, with no problems. Among them, the surface treatment and heat treatment are preferable because it is easy to control various characteristics and those are superior in productivity.

Specific examples of the surface treating method of the (d) acid reactive glass powder include washing with acid such as phosphoric acid or acetic acid, surface treatment with acidity compound such as tartaric acid or polycarboxylic acid, surface treatment with fluoride such as aluminum fluoride and surface treatment with silane compound such as γ-mercaptopropyl trimethoxy silane or tetramethoxy silane.

The surface treating method which can be used in the present disclosure is not limited the above described method and these surface treating methods can be used alone, or in a combination thereof.

Specific examples of the heat treating method of the (d) acid reactive glass powder include a treating method which includes heating for a range of 1 hour to 72 hours within a range of 100° C. to 800° C. using electric furnace. The heat treating method which can be used in the present disclosure is not limited the above described method and uni-processing or multi-stage processing can be used with respect to the treatment process.

It is preferable that a content of the (d) acid-reactive glass powder is within a range of 60 to 80 wt. % based on the whole dental glass ionomer cement composition. When the content of the (d) acid-reactive glass powder is less than 60 wt. %, there is a case where the mechanical characteristic decrease. When the content of the (d) acid-reactive glass powder exceeds 80 wt. %, there is a case that viscosity of the mixed material becomes higher to worsen operability. Further there is a case where operation time may become short.

A polybasic carboxylic acid, a phosphoric acid, a pyrophosphoric acid or a tripolyphosphoric acid and the like may be contained in the dental glass ionomer cement composition of the present disclosure, for the purpose of adjusting the operation time and setting time. Specific examples of the polybasic carboxylic acid used in the dental glass ionomer cement composition of the present disclosure include tartaric acid, citric acid, maleic acid, fumaric acid, malic acid, aconitic acid, tricarballylic acid, itaconic acid, 1-butene-1,2,4-tricarboxylic acid, and 3-butene-1,2,3-tricarboxylic acid, and the like. The aforementioned polybasic carboxylic acid are not limited to these, but can be used without any limitation. A polybasic carboxylic acid, a phosphoric acid, a pyrophosphoric acid and/or a tripolyphosphoric acid may be used alone or in combination of two or more thereof. A content of a polybasic carboxylic acid, a phosphoric acid, a pyrophosphoric acid and/or a tripolyphosphoric acid is preferably within a range of 0.1 to 15.0 wt. % based on the whole dental glass ionomer cement composition.

Further, a surfactant can be contained in the dental glass ionomer cement composition of the present disclosure to such a range that various properties are not influenced, for the purpose of improving mixability. The surfactant which can be used in the dental glass ionomer cement composition of the present disclosure may be any of an ionic surfactant and a nonionic surfactant.

Specific examples of the anionic surfactant in the ionic surfactant include aliphatic carboxylic acid metal salts such as sodium stearate, sulfated aliphatic carboxylic acid metal salts such as sodium dioctyl sulfosuccinate, and metal salts of higher alcohol sulfate ester such as sodium stearyl sulfate. In addition, examples of the cationic surfactant include an adduct of higher alkylamine and ethylene oxide, amines made from lower amine, and alkyltrimethylammonium salts such as lauryltrimethylammoniun chloride. Further, examples of the amphoteric surfactant include metal salts of higher alkylaminopropionic acid such as sodium stearylaminopropionate, and betaines such as lauryldimethylbetaine.

Examples of the nonionic surfactant include polyethylene glycol type and polypropylene glycol type in which ethylene oxide or propylene oxide is added to higher alcohols, alkyl phenols, fatty acids, higher fatty amines, or aliphatic amides, and polyhydric alcohol type in which polyhydric alcohols, diethanolamines, or saccharides is ester bonded to a fatty acid.

The aforementioned surfactants are not limited to these, but can be used without any limitation. These surfactants can be used alone or in a combination of a few kinds.

It is preferable that a content of surfactant contained in the dental glass ionomer cement composition of the present disclosure is within a range of 0.001 to 5 wt. % based on the whole dental glass ionomer cement composition.

Further, when the dental glass ionomer cement composition of the present disclosure includes a paste form, a thickener can be contained to such a range that various properties are not influenced, for the purpose of improving paste property.

The dental glass ionomer cement composition of the present disclosure can be use an inorganic thickener and an organic thickener as the thickener. Specific examples of an inorganic thickener include fumed silica, calcium carbonate, calcium silicate, magnesium silicate, and a clay mineral such as saponite, montmorillonite, beidellite, vermiculite, sauconite, stevensite, hectorite, smectite, nekutaito and sepiolite.

Specific examples of an organic thickener include methyl cellulose, hydroxyethyl cellulose, hydroxymethyl cellulose, hydroxypropyl cellulose, carboxymethyl cellulose, carboxymethyl cellulose sodium, carboxymethyl cellulose calcium, carboxypolymethylene, sodium alginate, propylene glycol alginate ester, sodium polyacrylate, starch, starch sodium glycolate, starch phosphate ester, polyvinyl pyrrolidone, carboxyvinyl polymer, khaya gum, arabic gum, karaya gum, guar gum. These thickeners may be used alone or as a mixture of two or more thereof.

It is preferable that the content of the thickener of the present disclosure is within a range of 0.001 to 10 wt. % based on the whole dental glass ionomer cement composition.

Further, a non acid-reactive powder can be contained in the dental glass ionomer cement composition of the present disclosure to such a range that various properties are not influenced, for the purpose of adjusting operability, a mechanical characteristic or a curing characteristic.

As the non acid-reactive powder used in the dental glass ionomer cement composition of the present disclosure, any non acid-reactive powder as long as the non acid-reactive powder does not contain element which may form chelate-bond with an acid group of the non-crosslinked polyalkenoic acid can be used without any limitation.

Examples of the non acid-reactive powder include known dental fillers such as an inorganic filler, an organic filler and an organic-inorganic composite filler, and these can be used alone or in a combination of a few of them without any limitation. Among them, it is especially preferable that an inorganic filler is used. In addition, a shape of these non acid-reactive powder is not particularly limited, but arbitral particle shapes such as spherical, needle-like, plate-like, ground-like, and scaly-shapes and aggregate thereof may be used. An average particle diameter of the non acid-reactive powder is not particular limited, but is preferably within a range of 0.001 to 30 μm.

Specific examples of the inorganic filler include quartz, amorphous silica, ultrafine silica, various glasses which does not contain element which may form chelate-bond with an acidic group or alkaline metal salt of an acidic group (including a glass by melting method, a glass produced by a vapor phase reaction, synthetic glass by sol-gel method and the like), silicon nitride, silicon carbide, boron carbide and the like, but is not limited thereto.

It is preferable that a content of the non-acid reactive powder contained in the dental glass ionomer cement composition of the present disclosure is within a range of 0.001 to 30 wt. % based on the whole dental glass ionomer cement composition.

The dental glass ionomer cement composition of the present disclosure is provided in various forms such as powder/liquid material, paste/liquid material, and paste/paste, unless the (a) non-crosslinked polyalkenoic acid and/or the (c) crosslinked polyalkenoic acid coexist with (d) acid-reactive glass powder in the presence of the (b) water.

Specific examples of the form of the powder/liquid material include a combination of a powder containing the (c) crosslinked polyalkenoic acid and the (d) acid-reactive glass powder, and a liquid material containing the (a) non-crosslinked polyalkenoic acid and the (b) water, a combination of a powder containing the (d) acid-reactive glass powder and a liquid material containing the (a) non-crosslinked polyalkenoic acid, the (b) water and the (c) crosslinked polyalkenoic acid, a combination of a powder containing the (a) non-crosslinked polyalkenoic acid and the (d) acid-reactive glass powder, and a liquid material containing the (b) water and the (c) crosslinked polyalkenoic acid, and a combination of a powder containing the (a) non-crosslinked polyalkenoic acid, the (c) crosslinked polyalkenoic acid and the (d) acid-reactive glass powder, and a liquid material containing the (b) water, but not limited thereto.

Specific examples of the form of the paste/liquid material include a combination of a paste containing the (b) water and the (d) acid-reactive glass powder, and a liquid material containing the (a) non-crosslinked polyalkenoic acid, the (b) water and the (c) crosslinked polyalkenoic acid, but not limited thereto.

Specific examples of the form of the paste/paste include a combination of a first paste containing the (b) water and the (d) acid-reactive glass powder, and a second paste containing the (a) non-crosslinked polyalkenoic acid, the (b) water and the (c) crosslinked polyalkenoic acid, but not limited thereto.

Furthermore, the dental glass ionomer cement composition of the present disclosure may optionally contain other conventionally known additives such as preservatives, antimicrobial materials, and coloring pigments.

Examples

The present disclosure is described in more detail and specifically with reference to Examples. However, the present disclosure is not limited to Examples. Test methods for evaluating performances of the dental glass ionomer cement composition prepared in each of Examples and Comparative Examples are as follows.

Compressive Strength

A compressive strength was measured by the following procedures according to ISO 9917-1:2007. Under the environment of 23° C. and 50% of humidity, each of the dental glass ionomer cement composition of the examples of the present disclosure and comparative examples was prepared by mixing each component at the ratio shown in Examples. The prepared mixture was filled in a stainless steel mold (4φ×6 mm: cylindrical shape) and left in a 37° C. and 100% thermohygrostat for 1 hour. After 1 hour, the test specimen was removed from the mold and immersed in ion-exchanged water at 37° C. The specimen was taken out from the mold after 24 hours from the completion of mixing and an Instron universal tester (Instron 5567A manufactured by Instron) was used to measure the compressive strength at a crosshead speed of 1 mm/min.

Net Setting Time

Net setting time was measured by the following procedure according to ISO 9917-1: 2007. Under the environment of 23° C. and 50% of humidity, each of the dental glass ionomer cement composition of the examples of the present invention and comparative examples was prepared by mixing each component at the ratio shown in Examples. The prepared mixture was filled in an aluminum mold (length 8 mm×width 10 mm×height 5 mm). After 60 seconds from the end of mixing, the aluminum steel mold filled with the mixture was placed on a metal block (minimum size: 8 mm×75 mm×100 mm) in a thermohygrostat of 37° C. and 100% of humidity. Vicat needle (mass: 400±5 g, end diameter: 1.0±0.1 mm) was vertically taken down on the horizontal plane of the mixture and vestige of the vicat needle was visually observed. This operation was repeated until vestige of vicat needle did not show a perfect circle. Net setting time was set to time from the end of mixing to the time wherein vestige of vicat needle did not show a perfect circle.

Working Time

Under the environment of 23° C. and 50% of humidity, each of the dental glass ionomer cement composition of the examples of the present invention and comparative examples was prepared by mixing each component at the ratio shown in Examples. After mixing, the fluidity of the prepared mixture was confirmed by using spatula. Working time was set to time from the start of mixing to the time wherein the mixture became less fluid and filling (or luting) and shaping became impossible.

The components and the abbreviations thereof used for preparation of the dental glass ionomer cement composition in Examples and Comparative Examples are shown below.

(a) Non-Crosslinked Polyalkenoic Acid

AA1: acrylic acid homopolymer powder 1(weight average molecular weight: 20,000)
AA2: acrylic acid homopolymer powder 2 (weight average molecular weight: 50,000)
AA3: acrylic acid homopolymer powder 3 (weight average molecular weight: 100,000)
PCA1: acrylic acid-tricarboxylic acid copolymer powder 1 (weight average molecular weight: 80,000)
PCA2: acrylic acid-tricarboxylic acid copolymer powder 2 (weight average molecular weight: 140,000)
PCA3: acrylic acid-tricarboxylic acid copolymer powder 3 (weight average molecular weight: 250,000)
PCA4: acrylic acid-tricarboxylic acid copolymer powder 4 (weight average molecular weight: 320,000)

(b) Water

IEW: ion exchanged water (c) Crosslinked Polyalkenoic Acid

C1: crosslinked polyacrylic acid 1 (alkenoic acid: acrylic acid, cross-linking agent: diethylene glycol diallyl ether (0.05 wt. % with respect to acrylic acid))

C2: crosslinked polyacrylic acid 2 (alkenoic acid: acrylic acid, cross-linking agent: diethylene glycol diallyl ether (0.5 wt. % with respect to acrylic acid))
C3: crosslinked polyacrylic acid 3 (alkenoic acid: acrylic acid, cross-linking agent: diethylene glycol diallyl ether (1.0 wt. % with respect to acrylic acid))

(d) Acid-Reactive Glass Powder

G1: acid reactive glass powder 1 (fluoro-aluminosilicate glass, 50% average particle diameter: 3.2 μm)
G2: acid reactive glass powder 2 (fluoro-aluminosilicate glass, 50% average particle diameter: 4.7 μm)

G1: Preparation of Acid-Reactive Glass Powder 1

After mixing at a ratio of 23 wt. % of silica, 8 wt. % of aluminum oxide, 13 wt. % of aluminum phosphate, 14 wt. % of aluminum fluoride, and 42 wt. % strontium carbonate, the mixed material was molten at 1400° C. in a melting furnace. The melt was taken out from the melting furnace and was quenched in water to prepare a glass. The resulting glass was pulverized to obtain acid-reactive glass powder 1. The acid reactive glass powder was measured for an average particle diameter by a laser diffraction type grain size measuring apparatus (Microtrac MT3300EXII: NIKKISO Co., Ltd.). The result was 3.4 μm.

G2: Preparation of Acid-Reactive Glass Powder 2

Acid-reactive glass powder 2 was prepared by the same method as the acid-reactive glass powder 1 except that the average particle size was 4.7 μm by adjusting the pulverization time.

Other Component

TA: Tartaric acid

Preparation of Powder and Liquid Material

Liquid materials L1 to L11 were prepared by mixing each component according to each ratio shown in Table 1. Further, powders P1 to P12 were prepared by mixing each component according to each ratio shown in Table 2. The dental glass ionomer cement compositions (Examples 1 to 23 and Comparative Examples 1 to 3) prepared by mixing the combination of these powders and liquid materials at the powder/liquid ratio were evaluated for Compressive strength, Net setting time and Working time according to the above described method.

TABLE 1

Liquid material composition

Unit: wt. %

| | | L1 | L2 | L3 | L4 | L5 | L6 | L7 | L8 | L9 | L10 | L11 |
|---|---|---|---|---|---|---|---|---|---|---|---|---|
| (a) non-crosslinked polyalkenoic acid | AA1 | 40.00 | — | — | — | — | — | — | — | — | — | — |
| | AA2 | — | 40.00 | — | — | — | — | — | — | — | — | — |
| | AA3 | — | — | 40.00 | — | — | — | — | — | — | — | — |
| | PCA1 | — | — | — | 40.00 | — | — | — | — | — | — | — |
| | PCA2 | — | — | — | — | 40.00 | — | — | 25.00 | 10.00 | — | — |
| | PCA3 | — | — | — | — | — | 40.00 | — | — | — | 50.00 | — |
| | PCA4 | — | — | — | — | — | — | 40.00 | — | — | — | — |
| (b) Water | IEW | 60.00 | 60.00 | 60.00 | 50.00 | 60.00 | 60.00 | 60.00 | 65.00 | 85.00 | 50.00 | 60.00 |
| (c) Crosslinked polyalkenoic acid | C1 | — | — | — | — | — | — | — | — | — | — | 40.00 |
| Other component | TA | — | — | — | 10.00 | — | — | — | 10.00 | 5.00 | — | — |
| Total | | 100.00 | 100.00 | 100.00 | 100.00 | 100.00 | 100.00 | 100.00 | 100.00 | 100.00 | 100.00 | 100.00 |

TABLE 2

Powder composition

Unit: wt. %

| | | P1 | P2 | P3 | P4 | P5 | P6 | P7 | P8 | P9 | P10 | P11 | P12 |
|---|---|---|---|---|---|---|---|---|---|---|---|---|---|
| (c) Crosslinked polyalkenoic acid | C1 | 0.02 | 0.10 | 1.00 | 13.00 | — | — | — | — | 0.07 | 0.14 | 4.20 | 7.00 |
| | C2 | — | — | — | — | 1.00 | — | — | — | — | — | — | — |
| | C3 | — | — | — | — | — | 1.00 | 15.00 | — | — | — | — | — |
| (d) Acid-reactive glass powder | G1 | 99.98 | 99.90 | 99.00 | — | — | 99.00 | 85.00 | 100.00 | 99.93 | 99.86 | 95.80 | 93.00 |
| | G2 | — | — | — | 87.00 | 99.00 | — | — | — | — | — | — | — |
| Total | | 100.00 | 100.00 | 100.00 | 100.00 | 100.00 | 100.00 | 100.00 | 100.00 | 100.00 | 100.00 | 100.00 | 100.00 |

Table 3 shows evaluation results of the dental glass ionomer cement compositions shown in Examples 1 to 7 and Comparative Examples 1 to 3.

In the Example 1, high compressive strength was exhibited and the dental glass ionomer cement had preferable characteristics for setting time and working time.

The composition of the Example 2 was mixed by using the Liquid material L8 (containing 25 wt. % of the acrylic acid-tricarboxylic acid copolymer powder 2 having weight average molecular weight: 140,000 and 10 wt. % of tartaric acid) instead of the Liquid material L4 (containing 40.00 wt. % of the acrylic acid-tricarboxylic acid copolymer powder 1 having weight average molecular weight: 80,000 and 10 wt. % of tartaric acid) in the Example 1, at 4.0/1.0 of the powder/liquid ratio.

The composition of the Example 3 was mixed by using the Liquid material L9 (containing 10 wt. % of the acrylic acid-tricarboxylic acid copolymer powder 2 having weight average molecular weight: 140,000 and 5 wt. % of tartaric acid) instead of the Liquid material L4 (containing 40.00 wt. % of the acrylic acid-tricarboxylic acid copolymer powder 1 having weight average molecular weight: 80,000 and 10 wt. % of tartaric acid) in the Example 1, at 4.0/1.0 of the powder/liquid ratio.

The composition of the Example 4 was mixed by using the Liquid material L10 (containing 50 wt. % of the acrylic acid-tricarboxylic acid copolymer powder 3 having weight average molecular weight: 250,000) instead of the Liquid material L4 (containing 40.00 wt. % of the acrylic acid-tricarboxylic acid copolymer powder 1 having weight average molecular weight: 80,000 and 10 wt. % of tartaric acid) in the Example 1, at 1.5/1.0 of the powder/liquid ratio.

The composition of the Example 5 was mixed by using the Liquid material L8 (containing 25 wt. % of the acrylic acid-tricarboxylic acid copolymer powder 2 having weight average molecular weight: 140,000 and 10 wt. % of tartaric acid) instead of the Liquid material L4 (containing 40.00 wt. % of the acrylic acid-tricarboxylic acid copolymer powder 1 having weight average molecular weight: 80,000 and 10 wt. % of tartaric acid) in the Example 1, at 1.6/1.0 of the powder/liquid ratio.

The composition of the Example 6 was mixed by changing the powder/liquid ratio from 2.5/1.0 in Example 1 to 5.0/1.0.

The composition of the Example 7 was mixed by changing the powder/liquid ratio from 2.5/1.0 in Example 1 to 0.8/1.0.

parative Example 1, it was confirmed that although good setting time and working time were exhibited, the compressive strength was low.

The composition of the Comparative Example 2 was mixed by using the Powder P7 (containing the acid reactive glass powder 1 having 50% average particle diameter: 3.2 µm as the main component and 15.00 wt. % of crosslinked polyacrylic acid 3) instead of the powder P2 (containing the acid reactive glass powder 1 having 50% average particle diameter: 3.2 µm as the main component and 0.10 wt. % of crosslinked polyacrylic acid 1) in the Example 1. In Comparative Example 2, it was confirmed that although good setting time was exhibited, working time was short and the compressive strength was low.

The composition of the Comparative Example 3 was mixed by using the Powder P8 (containing the acid reactive glass powder 1 having 50% average particle diameter: 3.2 µm as the main component and not containing crosslinked polyalkenoic acid) instead of the powder P2 (containing the acid reactive glass powder 1 having 50% average particle diameter: 3.2 µm as the main component and 0.10 wt. % of crosslinked polyacrylic acid 1) in the Example 1 and using the Liquid material L11 (containing 40.00 wt. % of acrylic acid-tricarboxylic acid copolymer powder 1 and 0.05 wt. % of cross-linking agent based on the acrylic acid) instead of the Liquid material L4 (containing 40.00 wt. % of acrylic acid-tricarboxylic acid copolymer powder 1 having weight average molecular weight: 80,000 and 10 wt. % of tartaric acid) in the Example 1. In Comparative Example 3, it was confirmed that although good setting time was exhibited, working time was short and the compressive strength was low.

TABLE 3

Combination and Evaluation result of Examples 1 to 7 and Comparative Examples 1 to 3

| | | Example 1 | Example 2 | Example 3 | Example 4 | Example 5 | Example 6 | Example 7 | Comparative Example 1 | Comparative Example 2 | Comparative Example 3 |
|---|---|---|---|---|---|---|---|---|---|---|---|
| Powder | | P2 | P2 | P2 | P2 | P2 | P2 | P2 | P8 | P7 | P8 |
| Liquid material | | L4 | L8 | L9 | L10 | L8 | L4 | L4 | L4 | L4 | L11 |
| Powder/liquid ratio | | 2.5/1.0 | 4.0/1.0 | 4.0/1.0 | 1.5/1.0 | 1.6/1.0 | 5.0/1.0 | 0.8/1.0 | 2.5/1.0 | 2.5/1.0 | 2.5/1.0 |
| (a) | PCA1 (wt. %) | 11.43 | — | — | — | — | 6.67 | 22.22 | 11.43 | 11.43 | — |
| | PCA2 (wt. %) | — | 5.00 | 2.00 | — | 9.62 | — | — | — | — | — |
| | PCA3 (wt. %) | — | — | — | 20.00 | — | — | — | — | — | — |
| (b) | IEW (wt. %) | 14.28 | 13.00 | 17.00 | 20.00 | 25.00 | 8.33 | 27.78 | 14.28 | 14.29 | 17.14 |
| (c) | C1 (wt. %) | 0.07 | 0.08 | 0.08 | 0.06 | 0.06 | 0.08 | 0.04 | — | — | 11.43 |
| | C3 (wt. %) | — | — | — | — | — | — | — | — | 10.71 | — |
| (d) | G1 (wt. %) | 71.36 | 79.92 | 79.92 | 59.94 | 61.47 | 83.25 | 44.40 | 71.43 | 60.71 | 71.43 |
| Other component | TA (wt. %) | 2.86 | 2.00 | 1.00 | — | 3.85 | 1.67 | 5.56 | 2.86 | 2.86 | — |
| Total | | 100.00 | 100.00 | 100.00 | 100.00 | 100.00 | 100.00 | 100.00 | 100.00 | 100.00 | 100.00 |
| Compressive strength/MPa | | 243 | 214 | 203 | 202 | 233 | 248 | 205 | 182 | 192 | 178 |
| Net setting time/minute | | 2.3 | 3 | 3.2 | 2 | 2.5 | 2.1 | 3.2 | 2.4 | 2.1 | 2 |
| Working time/minute | | 2.6 | 3.1 | 3.5 | 2.2 | 2.9 | 2 | 3.4 | 2.8 | 1.5 | 1.7 |

In the Examples 2 to 7, high compressive strength was exhibited and the dental glass ionomer cement had preferable characteristics for setting time and working time.

The composition of the Comparative Example 1 was mixed by using the Powder P8 (containing the acid reactive glass powder 1 having 50% average particle diameter: 3.2 µm as the main component and not containing crosslinked polyalkenoic acid) instead of the powder P2 (containing the acid reactive glass powder 1 having 50% average particle diameter: 3.2 µm as the main component and 0.10 wt. % of crosslinked polyacrylic acid 1) in the Example 1. In Com- Table 4 shows evaluation results of the dental glass ionomer cement compositions shown in Examples 8 to 12.

The composition of the Example 8 was mixed by using the Powder P1 (containing the acid reactive glass powder 1 having 50% average particle diameter: 3.2 µm as the main component and 0.02 wt. % of crosslinked polyacrylic acid 1) instead of the powder P2 (containing the acid reactive glass powder 1 having 50% average particle diameter: 3.2 µm as the main component and 0.10 wt. % of crosslinked polyacrylic acid 1) in the Example 1.

The composition of the Example 9 was mixed by using the Powder P3 (containing the acid reactive glass powder 1 having 50% average particle diameter: 3.2 μm as the main component and 1.00 wt. % of crosslinked polyacrylic acid 1) instead of the powder P2 (containing the acid reactive glass powder 1 having 50% average particle diameter: 3.2 μm as the main component and 0.10 wt. % of crosslinked polyacrylic acid 1) in the Example 1.

The composition of the Example 10 was mixed by using the Powder P4 (containing the acid reactive glass powder 2 having 50% average particle diameter: 4.7 μm as the main component and 13.00 wt. % of crosslinked polyacrylic acid 1) instead of the powder P2 (containing the acid reactive glass powder 1 having 50% average particle diameter: 3.2 μm as the main component and 0.10 wt. % of crosslinked polyacrylic acid 1) in the Example 1.

The composition of the Example 11 was mixed by using the Powder P5 (containing the acid reactive glass powder 2 having 50% average particle diameter: 4.7 μm as the main component and 1.00 wt. % of crosslinked polyacrylic acid 2) instead of the Powder P2 (containing the acid reactive glass powder 1 having 50% average particle diameter: 3.2 μm as the main component and 0.10 wt. % of crosslinked polyacrylic acid 1) in the Example 1.

The composition of the Example 12 was mixed by using the Powder PG (containing the acid reactive glass powder 1 having 50% average particle diameter: 3.2 μm as the main component and 1.00 wt. % of crosslinked polyacrylic acid 3) instead of the powder P2 (containing the acid reactive glass powder 1 having 50% average particle diameter: 3.2 μm as the main component and 0.10 wt. % of crosslinked polyacrylic acid 1) in the Example 1.

In the Examples 8 to 12, high compressive strength was exhibited and the dental glass ionomer cement had preferable characteristics for setting time and working time.

The composition of the Example 14 was mixed by using the Liquid material L2 (containing 40.00 wt. % of the acrylic acid homopolymer powder 2 having weight average molecular weight: 50,000) instead of the Liquid material L4 (containing 40.00 wt. % of the acrylic acid-tricarboxylic acid copolymer powder 1 having weight average molecular weight: 80,000 and 10 wt. % of tartaric acid) in the Example 1.

The composition of the Example 15 was mixed by using the Liquid material L3 (containing 40.00 wt. % of the acrylic acid homopolymer powder 3 having weight average molecular weight: 100,000) instead of the Liquid material L4 (containing 40.00 wt. % of the acrylic acid-tricarboxylic acid copolymer powder 1 having weight average molecular weight: 80,000 and 10 wt. % of tartaric acid) in the Example 1.

The composition of the Example 16 was mixed by using the Liquid material L5 (containing 40.00 wt. % of the acrylic acid-tricarboxylic acid copolymer powder 2 having weight average molecular weight: 140,000) instead of the Liquid material L4 (containing 40.00 wt. % of the acrylic acid-tricarboxylic acid copolymer powder 1 having weight average molecular weight: 80,000 and 10 wt. % of tartaric acid) in the Example 1.

The composition of the Example 17 was mixed by using the Liquid material L6 (containing 40.00 wt. % of the acrylic acid-tricarboxylic acid copolymer powder 3 having weight average molecular weight: 250,000) instead of the Liquid material L4 (containing 40.00 wt. % of the acrylic acid-tricarboxylic acid copolymer powder 1 having weight average molecular weight: 80,000 and 10 wt. % of tartaric acid) in the Example 1.

TABLE 4

Combination and Evaluation result of Examples 8 to 12

| | | Example 8 | Example 9 | Example 10 | Example 11 | Example 12 |
|---|---|---|---|---|---|---|
| Powder | | P1 | P3 | P4 | P5 | P6 |
| Liquid material | | L4 | L4 | L4 | L4 | L4 |
| Powder/liquid ratio | | 2.5/1.0 | 2.5/1.0 | 2.5/1.0 | 2.5/1.0 | 2.5/1.0 |
| (a) | PCA1 (wt. %) | 11.43 | 11.43 | 11.43 | 11.43 | 11.43 |
| (b) | IEW (wt. %) | 14.29 | 14.29 | 14.28 | 14.29 | 14.29 |
| (c) | C1 (wt. %) | 0.01 | 0.71 | 9.29 | — | — |
| | C2 (wt. %) | — | — | — | 0.71 | — |
| | C3 (wt. %) | — | — | — | — | 0.71 |
| (d) | G1 (wt. %) | 71.41 | 70.71 | — | — | 70.71 |
| | G2 (wt. %) | — | — | 62.14 | 70.71 | — |
| Other component | TA (wt. %) | 2.86 | 2.86 | 2.86 | 2.86 | 2.86 |
| Total | | 100.00 | 100.00 | 100.00 | 100.00 | 100.00 |
| Compressive strength/MPa | | 228 | 250 | 228 | 251 | 252 |
| Net setting time/minute | | 2.3 | 2.3 | 2.2 | 2.2 | 2.1 |
| Working time/minute | | 2.6 | 2.4 | 2.2 | 2.2 | 2.2 |

Table 5 shows evaluation results of the dental glass ionomer cement compositions shown in Examples 13 to 18.

The composition of the Example 13 was mixed by using the Liquid material L1 (containing 40.00 wt. % of the acrylic acid homopolymer powder 1 having weight average molecular weight: 20,000) instead of the Liquid material L4 (containing 40.00 wt. % of the acrylic acid-tricarboxylic acid copolymer powder 1 having weight average molecular weight: 80,000 and 10 wt. % of tartaric acid) in the Example 1.

The composition of the Example 18 was mixed by using the Liquid material L7 (containing 40.00 wt. % of the acrylic acid-tricarboxylic acid copolymer powder 4 having weight average molecular weight: 320,000) instead of the Liquid material L4 (containing 40.00 wt. % of the acrylic acid-tricarboxylic acid copolymer powder 1 having weight average molecular weight: 80,000 and 10 wt. % of tartaric acid) in the Example 1.

In the Examples 13 to 18, high compressive strength was exhibited and the dental glass ionomer cement had preferable characteristics for setting time and working time.

TABLE 5

Combination and Evaluation result of Examples 13 to 18

|  |  | Example 13 | Example 14 | Example 15 | Example 16 | Example 17 | Example 18 |
|---|---|---|---|---|---|---|---|
| Powder |  | P2 | P2 | P2 | P2 | P2 | P2 |
| Liquid material |  | L1 | L2 | L3 | L5 | L6 | L7 |
| Powder/liquid ratio |  | 2.5/1.0 | 2.5/1.0 | 2.5/1.0 | 2.5/1.0 | 2.5/1.0 | 2.5/1.0 |
| (a) | AA1 (wt. %) | 11.43 | — | — | — | — | — |
|  | AA2 (wt. %) | — | 11.43 | — | — | — | — |
|  | AA3 (wt. %) | — | — | 11.43 | — | — | — |
|  | PCA2 (wt. %) | — | — | — | 11.43 | — | — |
|  | PCA3 (wt. %) | — | — | — | — | 11.43 | — |
|  | PCA4 (wt. %) | — | — | — | — | — | 11.43 |
| (b) | IEW (wt. %) | 17.14 | 17.14 | 17.14 | 17.14 | 17.14 | 17.14 |
| (c) | C1 (wt. %) | 0.07 | 0.07 | 0.07 | 0.07 | 0.07 | 0.07 |
| (d) | G1 (wt. %) | 71.36 | 71.36 | 71.36 | 71.36 | 71.36 | 71.36 |
| Other component | TA (wt. %) | — | — | — | — | — | — |
| Total |  | 100 | 100 | 100 | 100 | 100 | 100 |
| Compressive strength/MPa |  | 211 | 237 | 245 | 244 | 250 | 251 |
| Net setting time/minute |  | 3 | 2.7 | 2.4 | 2.3 | 2.2 | 2.2 |
| Working time/minute |  | 3.2 | 3 | 2.8 | 2.6 | 2.5 | 2 |

Table 6 shows evaluation results of the dental glass ionomer cement compositions shown in Examples 19 to 23.

The composition of the Example 19 was mixed by changing the powder/liquid ratio from 2.5/1.0 in Example 1 to 4.0/1.0.

The composition of the Example 20 was mixed by using the Powder P9 (containing the acid reactive glass powder 1 having 50% average particle diameter: 3.2 μm as the main component and 0.08 wt. % of crosslinked polyacrylic acid 1) instead of the Powder P2 (containing the acid reactive glass powder 1 having 50% average particle diameter: 3.2 μm as the main component and 0.10 wt. % of crosslinked polyacrylic acid 1) in the Example 1.

The composition of the Example 21 was mixed by using the Powder P10 (containing the acid reactive glass powder 1 having 50% average particle diameter: 3.2 μm as the main component and 0.13 wt. % of crosslinked polyacrylic acid 1) instead of the Powder P2 (containing the acid reactive glass powder 1 having 50% average particle diameter: 3.2 μm as the main component and 0.10 wt. % of crosslinked polyacrylic acid 1) in the Example 1.

The composition of the Example 22 was mixed by using the Powder P11 (containing the acid reactive glass powder 1 having 50% average particle diameter: 3.2 μm as the main component and 4.00 wt. % of crosslinked polyacrylic acid 1) instead of the powder P2 (containing the acid reactive glass powder 1 having 50% average particle diameter: 3.2 Σm as the main component and 0.10 wt. % of crosslinked polyacrylic acid 1) in the Example 1.

The composition of the Example 23 was mixed by using the Powder P12 (containing the acid reactive glass powder 1 having 50% average particle diameter: 3.2 μm as the main component and 7.00 wt. % of crosslinked polyacrylic acid 1) instead of the Powder P2 (containing the acid reactive glass powder 1 having 50% average particle diameter: 3.2 μm as the main component and 0.10 wt. % of crosslinked polyacrylic acid 1) in the Example 1.

In the Examples 19 to 23, high compressive strength was exhibited and the dental glass ionomer cement had preferable characteristics for setting time and working time.

TABLE 6

Combination and Evaluation result of Examples 19 to 23

|  |  | Example 19 | Example 20 | Example 21 | Example 22 | Example 23 |
|---|---|---|---|---|---|---|
| Powder |  | P2 | P9 | P10 | P11 | P12 |
| Liquid material |  | L4 | L4 | L4 | L4 | L4 |
| Powder/liquid ratio |  | 4.0/1.0 | 2.5/1.0 | 2.5/1.0 | 2.5/1.0 | 2.5/1.0 |
| (a) | PCA1 (wt. %) | 8.00 | 11.43 | 11.43 | 11.43 | 11.43 |
| (b) | IEW (wt. %) | 10.00 | 14.29 | 14.29 | 14.29 | 14.29 |
| (c) | C1 (wt. %) | 0.08 | 0.05 | 0.10 | 3.00 | 5.00 |
| (d) | G1 (wt. %) | 79.92 | 71.37 | 71.32 | 68.42 | 66.42 |
| Other component | TA (wt. %) | 2.00 | 2.86 | 2.86 | 2.86 | 2.86 |
| Total |  | 100 | 100 | 100 | 100 | 100 |
| Compressive strength/MPa |  | 245 | 241 | 252 | 253 | 240 |
| Net setting time/minute |  | 2.3 | 2.6 | 2.4 | 2.4 | 2.2 |
| Working time/minute |  | 2.6 | 2.4 | 2.3 | 2.2 | 2.2 |

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

What is claimed is:

1. A dental glass ionomer cement composition, comprising
    (a) non-crosslinked polyalkenoic acid,
    (b) water,
    (c) crosslinked polyalkenoic acid: 0.01 to 10 wt. %, and
    (d) acid-reactive glass powder.

2. The dental glass ionomer cement composition of claim 1, wherein
    the (c) crosslinked polyalkenoic acid is a crosslinked polyacrylic acid.

3. The dental glass ionomer cement composition of claim 1, wherein
    (a) non-crosslinked polyalkenoic acid: 5 to 20 wt. %,
    (b) water: 10 to 25 wt. %,
    (c) crosslinked polyalkenoic acid: 0.01 to 10 wt. %, and
    (d) acid-reactive glass powder: 60 to 80 wt. %.

4. The dental glass ionomer cement composition of claim 2, wherein
    (a) non-crosslinked polyalkenoic acid: 5 to 20 wt. %,
    (b) water: 10 to 25 wt. %,
    (c) crosslinked polyalkenoic acid: 0.01 to 10 wt. %, and
    (d) acid-reactive glass powder: 60 to 80 wt. %.

* * * * *